US012616589B2

(12) United States Patent
Lipsey et al.

(10) Patent No.: US 12,616,589 B2
(45) Date of Patent: May 5, 2026

(54) SYSTEMS AND METHODS FOR AN ANKLE PROSTHESIS

(71) Applicant: Rehabilitation Institute of Chicago, Chicago, IL (US)

(72) Inventors: James Lipsey, Chicago, IL (US); Tom Pickerill, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 723 days.

(21) Appl. No.: 18/042,941

(22) PCT Filed: Aug. 31, 2021

(86) PCT No.: PCT/US2021/048387
§ 371 (c)(1),
(2) Date: Feb. 24, 2023

(87) PCT Pub. No.: WO2022/047364
PCT Pub. Date: Mar. 3, 2022

(65) Prior Publication Data
US 2023/0329885 A1 Oct. 19, 2023

Related U.S. Application Data

(60) Provisional application No. 63/072,717, filed on Aug. 31, 2020.

(51) Int. Cl.
*A61F 2/66* (2006.01)
*A61F 2/68* (2006.01)
*A61F 2/50* (2006.01)

(52) U.S. Cl.
CPC .............. *A61F 2/6607* (2013.01); *A61F 2/68* (2013.01); *A61F 2002/507* (2013.01)

(58) Field of Classification Search
CPC .. A61F 2/66; A61F 2/6607; A61F 2/68; A61F 2/70; A61F 2002/507; A61F 2002/6657
See application file for complete search history.

(56) References Cited

U.S. PATENT DOCUMENTS

2015/0230943 A1 8/2015 Marlin et al.
2018/0311837 A1 11/2018 Choi et al.

OTHER PUBLICATIONS

Patent Cooperation Treaty, International Search Report, International Application No. PCT/US2021/048387, date of mailing Dec. 8, 2021, 7 pages.
Lenzi, T. et al., "Design, Deveopment, and Validation of a Lightweight Non-Backdrivable Robotic Ankle Prosthesis," IEEE/ASME Transactions on Mechatronics, vol. 24, Issue 2, Jan. 11, 2019, pp. 471-482.

*Primary Examiner* — Brian A Dukert
(74) *Attorney, Agent, or Firm* — Polsinelli PC

(57) ABSTRACT

The ankle prosthesis of the present disclosure includes a load directing mechanism that alters the internal load path during weight bearing, guiding the load directly into the structural frame. By changing the load path with the load directing mechanism, both vertical and horizontal loads can be supported directly by the ankle's structure through a cam roller.

19 Claims, 10 Drawing Sheets

SYSTEMS AND METHODS FOR AN ANKLE PROSTHESIS

CROSS REFERENCE TO RELATED APPLICATIONS

The present PCT patent application claims the benefit of U.S. provisional patent application No. 63/072,717 filed on Aug. 31, 2020, which is hereby incorporated by reference to its entirety.

FIELD

The present disclosure generally relates to adaptive prosthetic devices; and in particular, to a system and associated method for an adaptive prosthetic ankle that re-directs a force onto a structural frame of the ankle to reduce a load on an actuator of the ankle.

BACKGROUND

Most commercially available lower limb prostheses are passive devices designed with constant or variable resistances at the joint level. They are lightweight, quiet and robust. They can be effective at activities such as level ground walking and standing, but provide limited function for other activities, such as stairs and ramps, getting into and out of a seated position and ensuring proper foot clearance to prevent falls. In these cases, the user must compensate for the lack of functionality.

Powered prostheses attempt to overcome these limitations by motorizing prosthetic joints to provide power generation and joint positioning. This enables the user to perform more activities. However, it comes at the cost of additional weight (2-4 times in many cases) plus the need to continuously charge batteries and noisy actuators. Existing powered devices use actuators that accommodate a wide range of speeds and torques to assist with a wide range of activities and require power over the course of an entire day. The devices consume power even during zero net energy tasks such as walking and standing. There is a need for lower limb prostheses that provide some of the most useful functions of existing powered devices, while keeping weight and size low enough to be useful for a wider range of amputees.

It is with these observations in mind, among others, that various aspects of the present disclosure were conceived and developed.

SUMMARY

In some examples, the present disclosure takes the form of a semi-active ankle prosthesis device comprising an ankle prosthesis including a structural frame, an ankle joint operatively mounted on the structural frame that pivots with respect to the structural frame about an ankle axis and a cam transmission including a cam follower, wherein the cam transmission pivots the ankle joint about the ankle axis. The ankle prosthesis further includes an actuator operatively coupled to the cam transmission to cause lateral translation of the cam transmission and a load directing mechanism defined along a cam roller of the cam transmission that directs a load imposed upon the ankle prosthesis into the structural frame during a loaded state, the load directing mechanism accommodating an unloaded state and a loaded state. In the unloaded state the cam roller is biased with an upward bias force applied in a first direction such that the cam roller contacts the cam follower and an air gap is defined between the cam roller and the structural frame, and in the loaded state the cam roller is compressed between the cam follower and the structural frame such that the load imposed upon the ankle prosthesis exceeding the upward bias force is directed into the structural frame. In some examples, the load directing mechanism includes a biasing component that biases the cam roller of the cam transmission against the cam follower of the cam transmission. In general, the proximal portion of the ankle prosthesis is configured for engagement (mounting or temporary connection) with a residual limb socket or other prosthetic component, and distal portion of the ankle prosthesis is configured for coupling to a prosthetic foot.

In some examples, the ankle prosthesis is an adaptive ankle prosthesis such that the ankle prosthesis regulates the ankle position only during non-weight bearing activities. Such an ankle prosthesis is actively positioned during walking to increase toe clearance, reducing the risk of trips and falls. It also adapts the ankle angle to different terrains, such as ramps and stairs, to provide more stability and comfort. It does not attempt to provide net-energy during weight bearing phases of gait, meaning the actuator's power requirements can be relaxed leading to a significantly lighter and smaller design.

In some examples, the present novel disclosure takes the form of a method of making an ankle prosthesis, comprising the steps of forming an ankle prosthesis, including providing a structural frame, mounting an ankle joint operatively along the structural frame that pivots with respect to the structural frame about an ankle axis, providing a cam transmission including a cam follower, wherein the cam transmission pivots the ankle joint about the ankle axis, operatively coupling an actuator to the cam transmission to cause lateral translation of the cam transmission, and forming a load directing mechanism defined along a cam roller of the cam transmission that directs a load imposed upon the ankle prosthesis into the structural frame during a loaded state, the load directing mechanism accommodating an unloaded state and a loaded state wherein in the unloaded state the cam roller is biased with an upward bias force applied in a first direction such that the cam roller contacts the cam follower and an air gap is defined between the cam roller and the structural frame, and wherein in the loaded state the cam roller is compressed between the cam follower and the structural frame such that the load imposed upon the ankle prosthesis exceeding the upward bias force is directed into the structural frame.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Various embodiments of an ankle prosthesis are described herein including a novel load-directing mechanism that alters an internal load path associated with a reaction torque about an ankle joint during weight bearing, guiding the internal load path away from an actuator of the ankle prosthesis and directly into a structural frame. This protects the actuator (including a leadscrew, supporting bearings and a motor) from otherwise very heavy loads associated with the reaction torque. In addition, due to the load directing mechanism, the associated actuator can fit a significantly smaller and lighter form factor. Initial studies have shown that the ankle prosthesis provides suitable function and mobility but in a form factor that is 50% shorter and 30% lighter than present technologies and provides a wider range of motion. The smaller build height and reduced weight allows more users to benefit from this technology and may help reduce prosthesis rejection rates due to fatigue.
Introduction An ankle prosthesis as described herein is a semi-active ankle prosthesis that regulates the ankle position only during non-weight bearing activities. Such an ankle prosthesis is actively positioned during walking to increase toe clearance, reducing the risk of trips and falls. It also adapts the ankle angle to different terrains, such as ramps and stairs, to provide more stability and comfort. It does not attempt to provide net-energy during weight bearing phases of gait, meaning the actuator's power requirements can be relaxed leading to a significantly lighter and smaller design.

Figure 1:
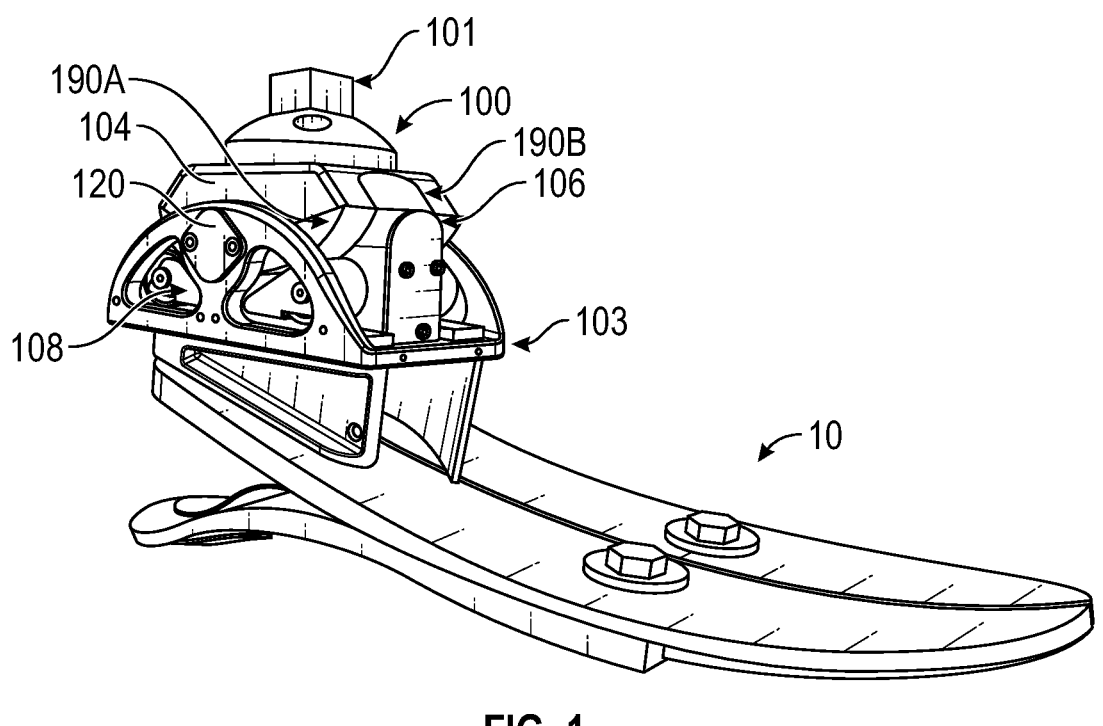
FIG. 1 is a perspective view showing an ankle prosthesis of the present application.
Figure 2A:
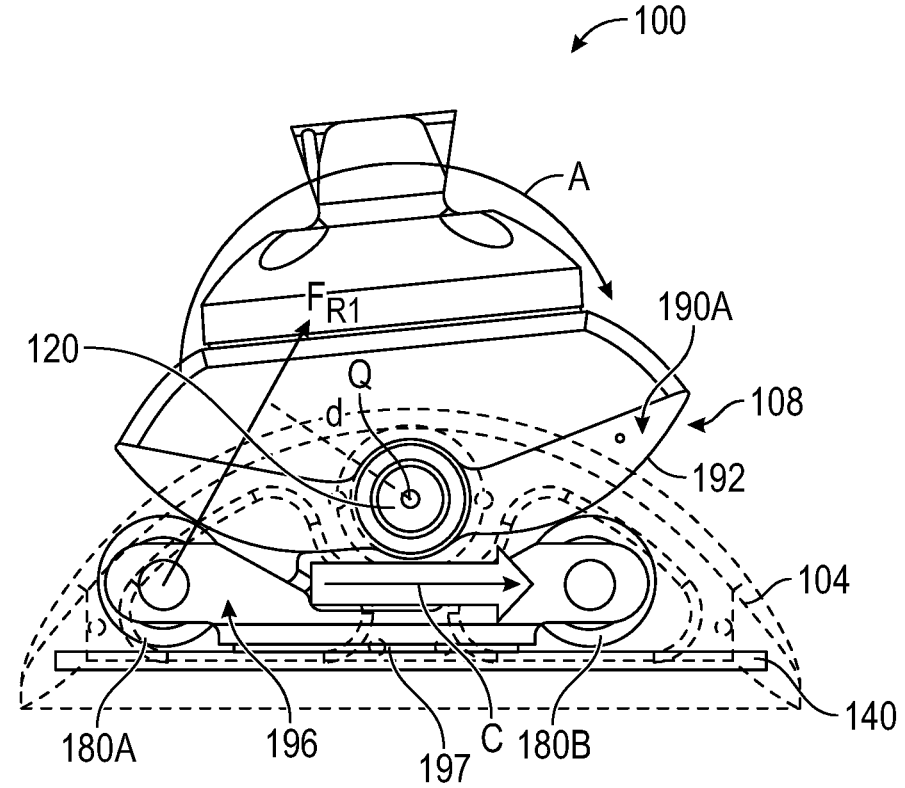
FIGS. 2A and 2B are side views showing a cam transmission of the ankle prosthesis of FIG. 1 showing action of forces when the ankle prosthesis is driven in either direction.

While positioning ankle flexion only during non-weight bearing tasks reduces the actuator's power requirements, the reaction torque that a prosthetic ankle needs to withstand under load is still very large. Typically, this means the actuation system used to position the ankle must be designed to withstand these loads. This adds a significant amount of weight and size, reducing the benefit of only positioning during non-weight bearing activities.
Mechanical System Referring to FIG. 1, one embodiment of an ankle prosthesis 100 is illustrated. In some embodiments, the ankle prosthesis 100 is an adaptive ankle prosthesis. As indicated, a proximal portion 101 of the ankle prosthesis 100 is configured for engagement (mounting or temporary connection) with a residual limb socket or other prosthetic component(s) (not shown), and a distal portion 103 of the ankle prosthesis 100 is coupled to a prosthetic foot 10. The ankle prosthesis 100 includes a structural frame 104, an ankle joint 120 operatively mounted on the structural frame 104, a cam transmission 108, an actuator 106 operatively coupled to the cam transmission 108, and a load directing mechanism 181 (FIG. 6) located within each cam roller 180A-D of a plurality of cam rollers 180A-D of the cam transmission 108. In some embodiments, the cam transmission 108 is a dual cam transmission. In particular, in some embodiments, the proximal portion 101 of the ankle prosthesis 100 is directly coupled to a pair of cam followers 190A and 190B of the cam transmission 108 and is further configured for rotation by the cam followers 190A and 190B about the ankle joint 120 defining an ankle axis Q (FIG. 2A).

Figures 8A, 8B:
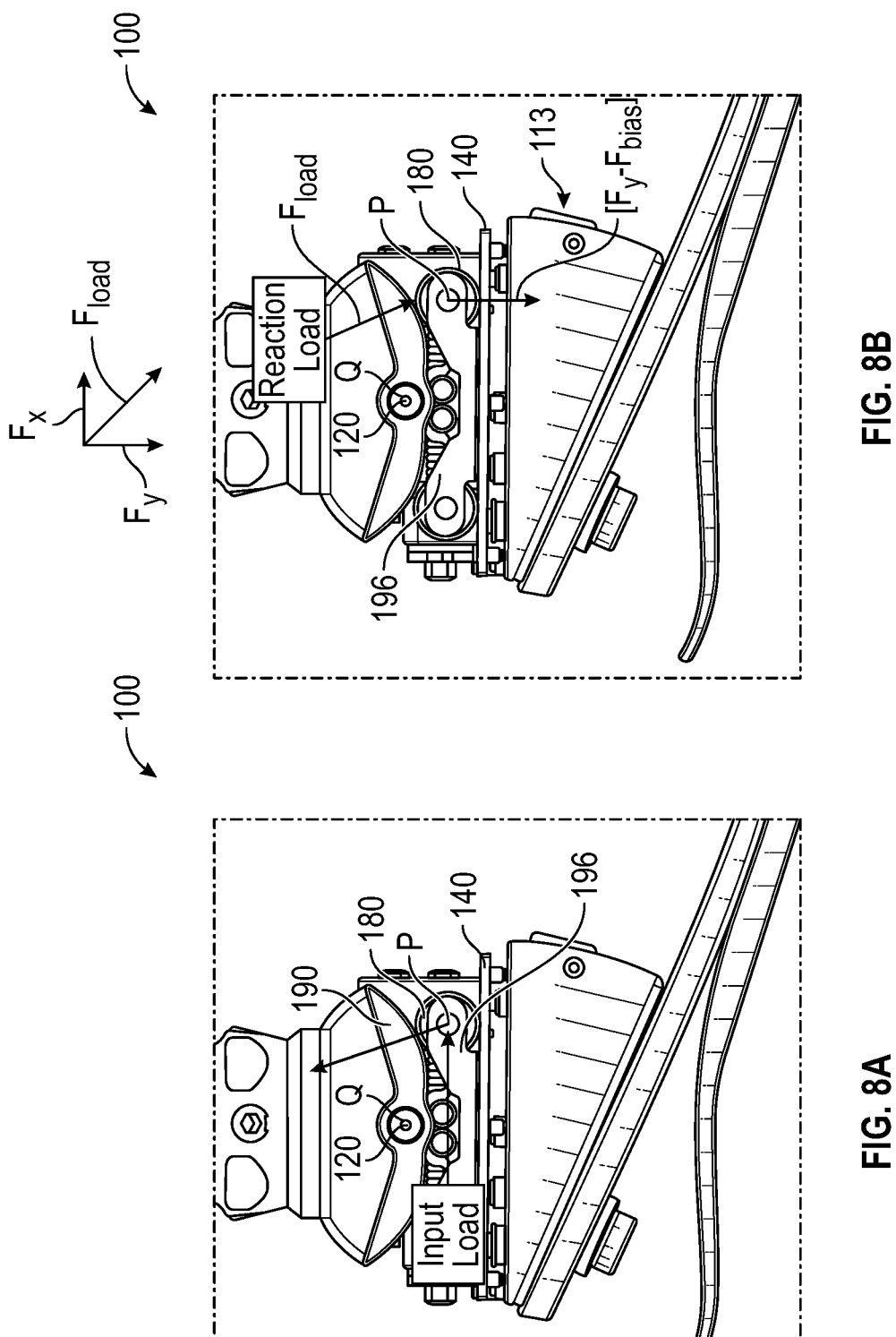
FIGS. 8A and 8B are a series of side views showing a path of the forces in the ankle shown in FIG. 1 when the ankle is in the unloaded state and in the loaded state.

In general, the load directing mechanism 181 of the ankle prosthesis 100 redirects a load path to accommodate both an unloaded state (FIG. 8A) and a loaded state (FIG. 8B) to reduce a load-bearing requirement of the actuator 106, and implementation of the load directing mechanism 181 results in a smaller size and weight profile of the ankle prosthesis 100. In the unloaded state of FIG. 8A, such as when the ankle is in free swing during a walk cycle or during some standing tasks, the actuator 106 is allowed to freely rotate the ankle joint 120 using the cam followers 190A and 190B and cam rollers 180A-D of the cam transmission 108 in a low-friction, low-stiffness path. In the loaded state of FIG. 8B, the ankle prosthesis 100 is directly bearing weight when a ground force $F_{base}$ is applied at a toe-end 113 of the ankle prosthesis 100 (e.g. when the associated foot 10 is "pushing off" of the ground during a walk cycle or when the wearer is leaning forward). The load-directing mechanism 181 enables the ankle prosthesis 100 to freely rotate or actively reposition about the ankle joint 120 when in the unloaded state, and to halt rotation about the ankle joint 120 when in the loaded state.

In the unloaded state shown in FIGS. 2A, 2B, 5B and 8A, the ankle prosthesis 100 is operable for active repositioning by the actuator 106 about the ankle joint 120 defining the ankle axis Q. The actuator 106 is allowed to pivot the cam followers 190A and 190B about the ankle joint 120 according to input from a controller (not shown) with little to no resistance from the plurality of cam rollers 180A-D. In particular, during the unloaded state, a biasing component 188 of the load directing mechanism 181 within each cam roller 180A-D applies an upward bias force $F_{bias}$ to each cam roller 180A-D in a first direction R. The plurality of cam rollers 180A-D are each allowed to rotate in the first or opposite second rotational direction A or B by the cam followers 190A and 190B as the actuator 106 translates the cam rollers 180A-D in a first or opposite second lateral direction C or D to cause rotation of the cam followers 190A and 190B in a first or opposite second rotational direction A or B about the ankle axis Q defined by the ankle joint 120. In particular, a trailing cam roller 180A/180B/180C/180D of the plurality of cam rollers 180A-D applies a first or second roller force $F_{R1}$ (FIG. 2A) or $F_{R2}$ (FIG. 2B) to a curved surface 192 of each respective cam follower 190A and 190B that in turn rotates the cam followers 190A and 190B in the first or opposite second rotational direction A or B about the ankle joint 120. It should be noted that the direction of rotation of the cam rollers 180A-D is opposite to the resultant direction of rotation of the cam followers 190A and 190B about the ankle joint 120. The upward bias force $F_{bias}$ applied to each cam roller 180A-D by the load directing mechanism 181 allows the cam rollers 180A-D to continually contact the cam followers 190A and 190B, forming an air gap between the cam rollers 180A-D and the structural frame 104 while in the unloaded state.

In contrast, in the loaded state shown in FIGS. 5C, 7A, 7B and 8B, the ground force $F_{base}$ induces a reaction torque FT about the ankle joint 120 and an associated load force $F_{Load}$ that is applied directly to the cam rollers 180A-D by the associated cam followers 190A and 190B. If this load force $F_{Load}$ exceeds the upward bias force $F_{bias}$, then the biasing component 188 of the load-directing mechanism 181 is compressed and the cam rollers 180A-D are forced downward against the structural frame 104 by the load force $F_{Load}$ applied by the cam followers 190. Friction between the cam followers 190A and 190B against the cam rollers 180A-D, and friction between the cam rollers 180A-D and the structural frame 104 prevents rotation of the cam followers 190A and 190B and cam rollers 180A-D, thus halting rotation about the ankle joint 120 when in the loaded state and directing the load force $F_{Load}$ away from the actuator 106 or other components of the ankle prosthesis 100.

Cam Transmission

Figure 2B:
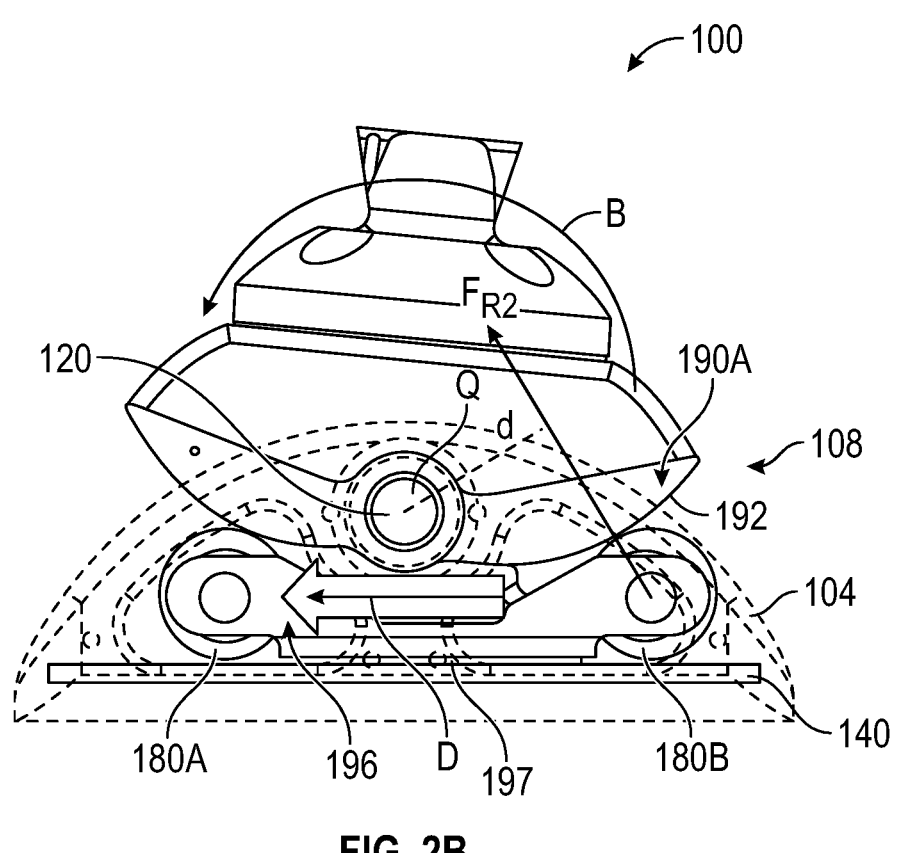
Figure 3:
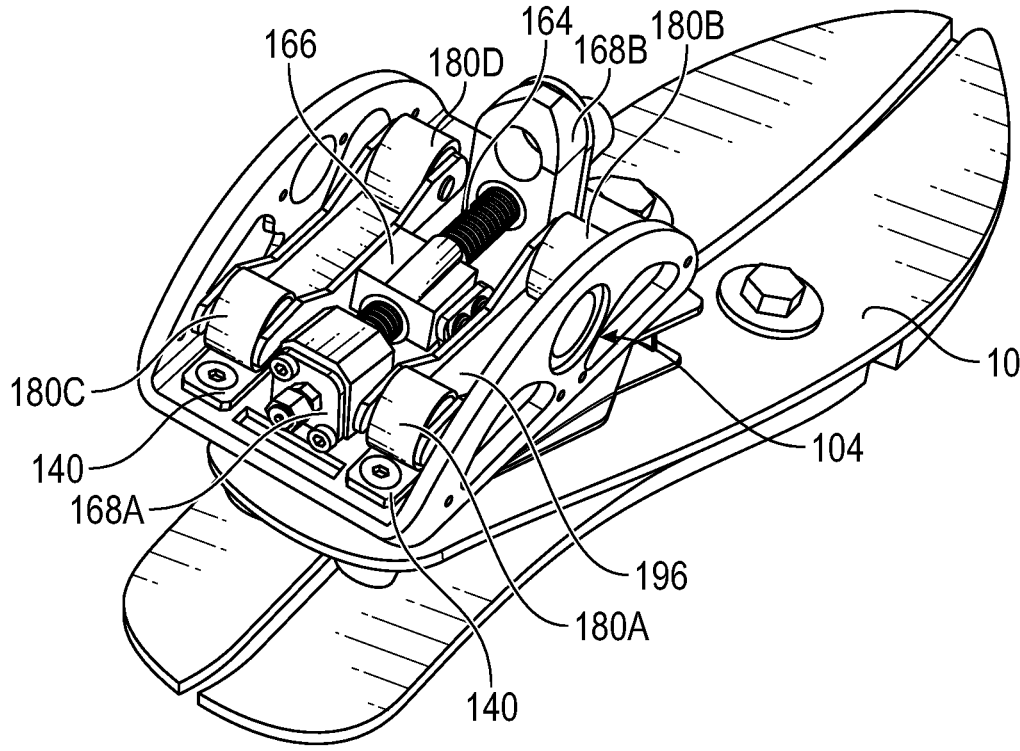
FIG. 3 is a perspective view showing a linear actuation system of the ankle prosthesis of FIG. 1 without a cam follower and motor.
Figure 4:
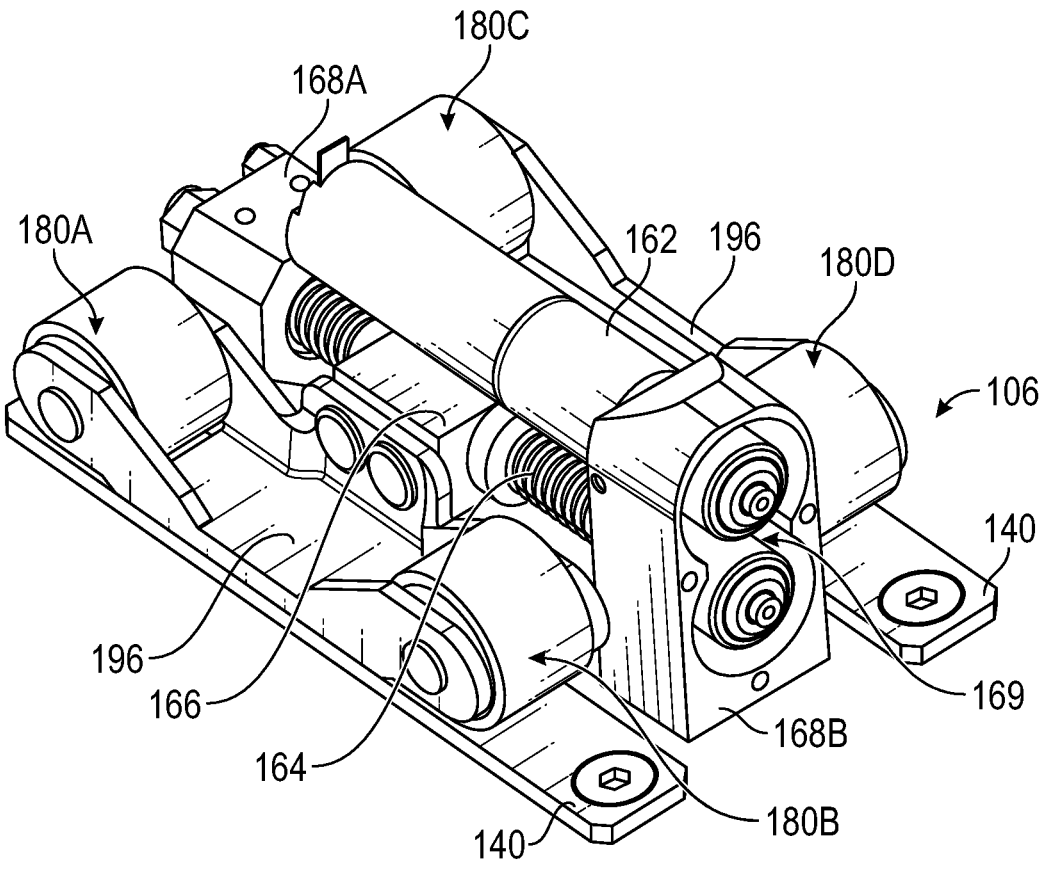
FIG. 4 is a perspective view showing the linear actuation system of the ankle prosthesis of FIG. 1 with the motor.

The ankle prosthesis 100 is rotated around the ankle axis Q to position the foot 10. As briefly discussed above, this is accomplished using the cam transmission 108 shown in FIGS. 2A, 2B and 7A. A simplified model showing a first half 108A of the cam transmission 108 in the unloaded state is illustrated, which includes a first cam roller 180A and an opposite second cam roller 180B of the plurality of cam rollers 180A-D and an associated first cam follower 190A. Note that the following discussion also applies to a second half 108B of the cam transmission 108 which includes a third cam roller 180C, a fourth cam roller 180D, and a second cam follower 190B of the pair of cam followers 190A and 190B. The cam rollers 180A and 180B are supported by a roller carrier 196 that is operable for translation in the first or opposite second lateral directions C or D. A horizontal force from the actuator 106 causes lateral translation of the roller carrier 196 and first and second cam rollers 180A and 180B; in other words, the roller carrier 196 and first and second cam rollers 180A and 180B move back and forth along a roller track 140 associated with the structural frame 104. In a preferred embodiment, the lateral translation of the roller carrier 196 is caused by the actuator 106 and induces a first or opposite second roller force $F_{R1}$ or $F_{R2}$. A trailing cam roller (180A in FIG. 2A, 180B in FIG. 2B) of the first and second cam rollers 180A and 180B directs the first or opposite second roller force $F_{R1}$ or $F_{R2}$ to the first cam follower 190A, which induces a moment about an axis of the cam follower 190 equal to the first or second roller force $F_{R1}$ or $F_{R2}$ multiplied by a normal distance to the axis (d). This moment causes the first cam follower 190A (and by result, the ankle joint 120) to pivot in the clockwise or counterclockwise direction A or B about the ankle axis Q. FIGS. 2A and 2B depict the ankle prosthesis 100 being driven in the direction shown by the respective curved arrow and the resulting load path in each instance.

Figure 7B:
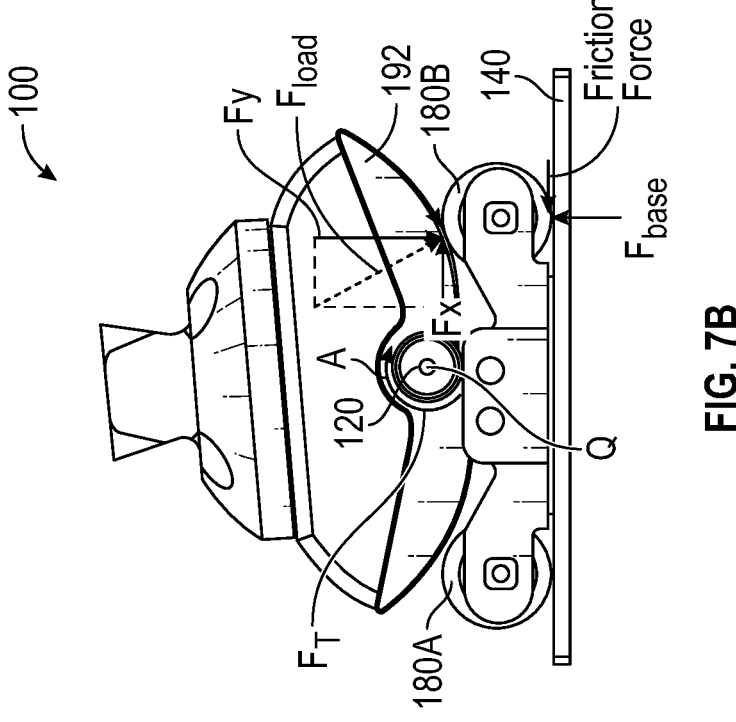
FIGS. 7A and 7B are a series of side views showing reaction forces on the ankle prosthesis of FIG. 1 when in a loaded position from ground-reaction forces.

In the loaded state shown in FIG. 7B, as discussed above, a vertical component $F_Y$ of the downward load force $F_{Load}$ induced on the cam followers 190A and 190B by the reaction torque $F_T$ is directed downwards towards the cam rollers 180A-D, forcing the cam rollers 180A-D downwards against the structural frame 104. Due to friction between the cam rollers 180A-D against the cam follower 190 and friction between the cam rollers 180A-D against the structural frame 104, rotation of the cam followers 190A and 190B about the ankle joint 120 is halted.

Actuation System

Referring to FIGS. 2A-4, the actuator 106 includes a motor 162 which transmits torque to a leadscrew 164 through a single 1:1 spur gear stage 169 in order to rotate the leadscrew 164 about a direction of elongation of the leadscrew 164. Rotating the leadscrew 164 in the unloaded state causes an associated leadscrew nut 166 to translate in the first or opposite second lateral direction C or D along the length of the leadscrew 164, and transmits an input torque applied to the leadscrew 164 by the motor 162 as an output force along a screw axis defined by a direction of elongation of the leadscrew 164. The leadscrew 164 is supported by a first support bearing 168A and a second support bearing 168B that sustain radial and axial forces, while reducing friction to increase efficiency. The leadscrew nut 166 is coupled to the roller carrier 196, which retain and ultimately transmit force to the plurality of cam rollers 180A-D.

Referring to FIG. 2A, the lateral movement of the roller carrier 196 in the first lateral direction C causes the first cam roller 180A to direct the first roller force $F_{R1}$ to the cam follower 190 in the opposite second lateral direction D such that the cam follower 190 is consequently rotated about the ankle joint 120 defining ankle axis Q in the first clockwise or counterclockwise direction A. Similarly, referring to FIG. 2B, the lateral movement of the roller carrier 196 in the opposite second lateral direction D causes the second cam roller 180B to direct the second roller force $F_{R2}$ to the cam follower 190 in the first lateral direction C such that the cam follower 190 is consequently rotated about the ankle axis Q in the opposite second clockwise or counterclockwise direction B. The leadscrew 164 is also non-backdriveable such that a force applied from the roller carrier 196 to the leadscrew nut 166 will not cause the leadscrew 164 to rotate or allow the leadscrew nut 166 to translate along the leadscrew 164.

Load Directing Mechanism

Figure 5A:
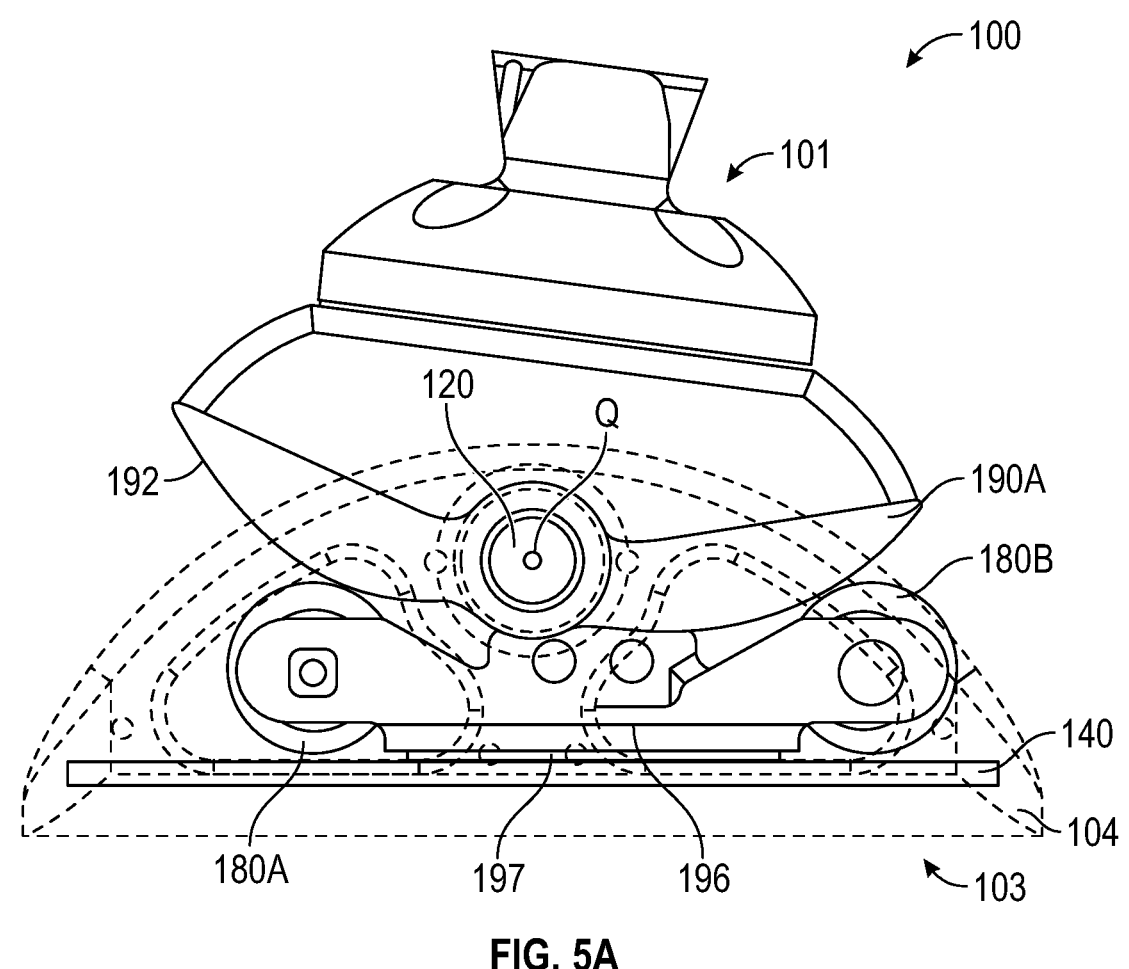
FIGS. 5A-5C are a series of side views showing a load directing mechanism of the ankle prosthesis of FIG. 1.
Figures 5B, 5C:
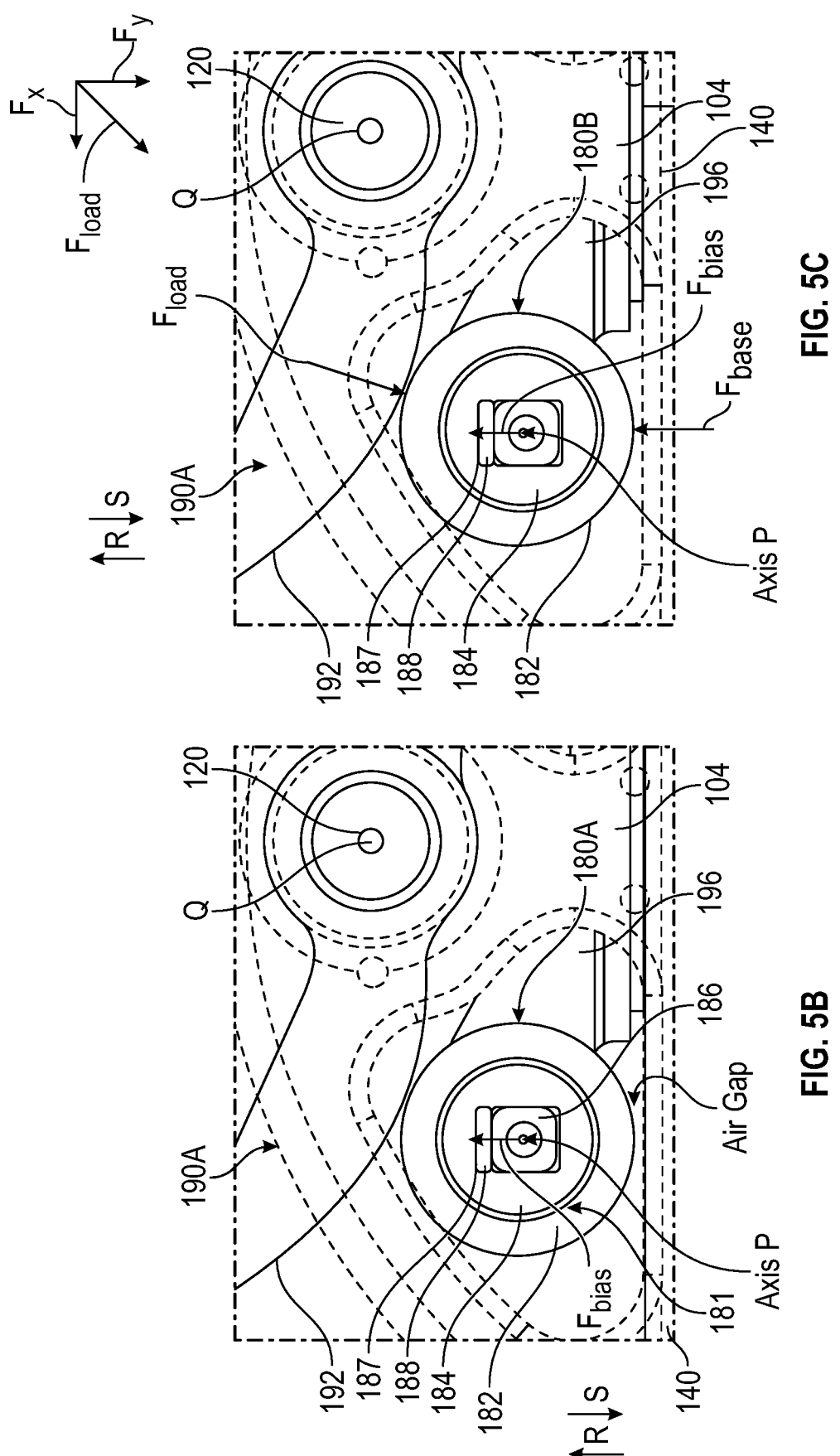
Figure 6:
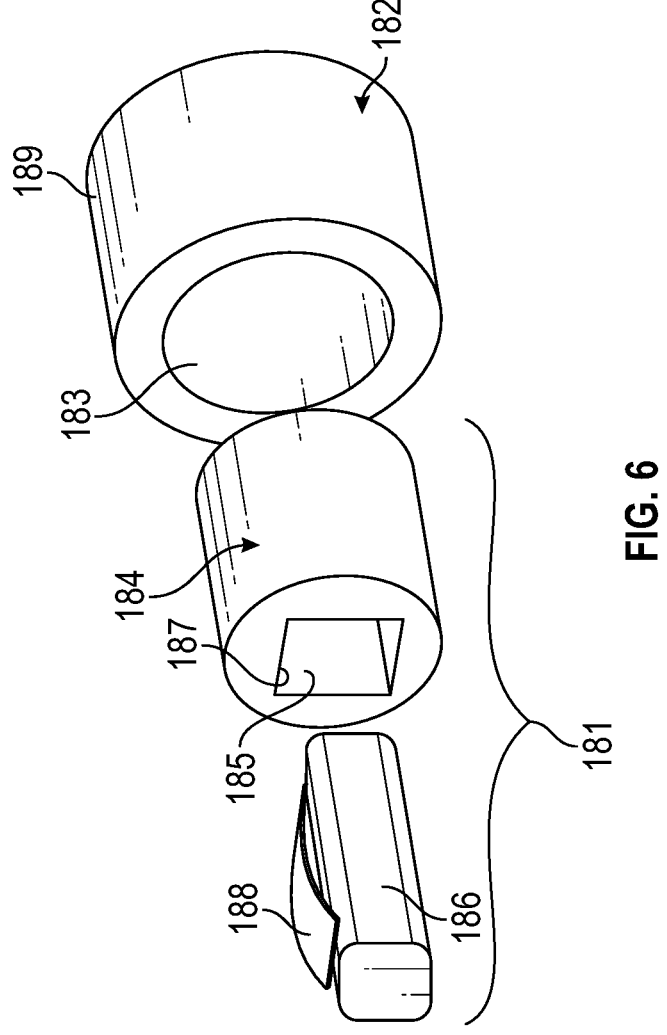
FIG. 6 is an exploded view showing the load directing mechanism of the ankle prosthesis of FIG. 1.

Referring to FIGS. 5A-7B, and in particular to FIGS. 5B-6, each cam roller 180A-D includes an outer roller 182 defining a roller channel 183 and a roller surface 189. In particular, each roller surface 189 can be a high-friction or otherwise gripping surface. Each load directing mechanism 181 is seated within the outer roller 182 of each cam roller 180A-D and includes a slider collar 184 with a rectangular slot 185 coaxially positioned within each roller channel 183, a shaft 186 defining a square profile housed within each rectangular slot 185, and a biasing component 188 positioned between the rectangular slot 185 and shaft 186. Such a loading mechanism 181 is provided in each cam roller 180A-D of the plurality of cam rollers 180A-D. The roller carrier 196 slides on the roller track 140, which is rigidly fixed to the structural frame 104. In some embodiments, the roller carrier 196 includes a linear bearing 197 between the roller carrier 196 and the roller track 140 that helps increase efficiency during lateral translation of the roller carrier 196. Each outer roller 182 of each respective cam roller 180A-D can spin freely on the associated slider collar 184, which in some embodiments is made of bearing bronze or other suitable low friction materials, further increasing efficiency. The slider collar 184 includes the rectangular slot 185 defined through a center of the slider collar 184 and slides vertically in the first or opposite second direction R or S onto the shaft 186 as shown in FIGS. 5B and 5C. The shaft 186 is rigidly fixed to the roller carrier 196. In an unloaded state (such as when the leg is in free swing and the foot is not in contact with the ground), shown in FIG. 5B, the slider collar 184 is biased upwardly in the first direction R by the biasing component 188. This ensures the cam rollers 180A-D are pre-loaded against the cam followers 190A and 190B and also ensures an air gap between the cam rollers 180A-D and the roller track 140. When the load on the ankle joint 120 is less than the pre-load determined by the biasing components 188 associated with each cam roller 180A-D, the force from the actuator 106 is transmitted solely to the cam followers 190A and 190B through the cam rollers 180A-D, inducing a moment and rotation about the ankle axis A of the ankle joint 120 (as shown in FIGS. 5C and 7B). Each cam roller 180A-D is allowed to rotate with the movement of the cam follower 190 unimpeded in the first or opposite second clockwise or counterclockwise direction A or B about a respective rotational roller axis P parallel to the ankle axis Q.

Figure 7A:
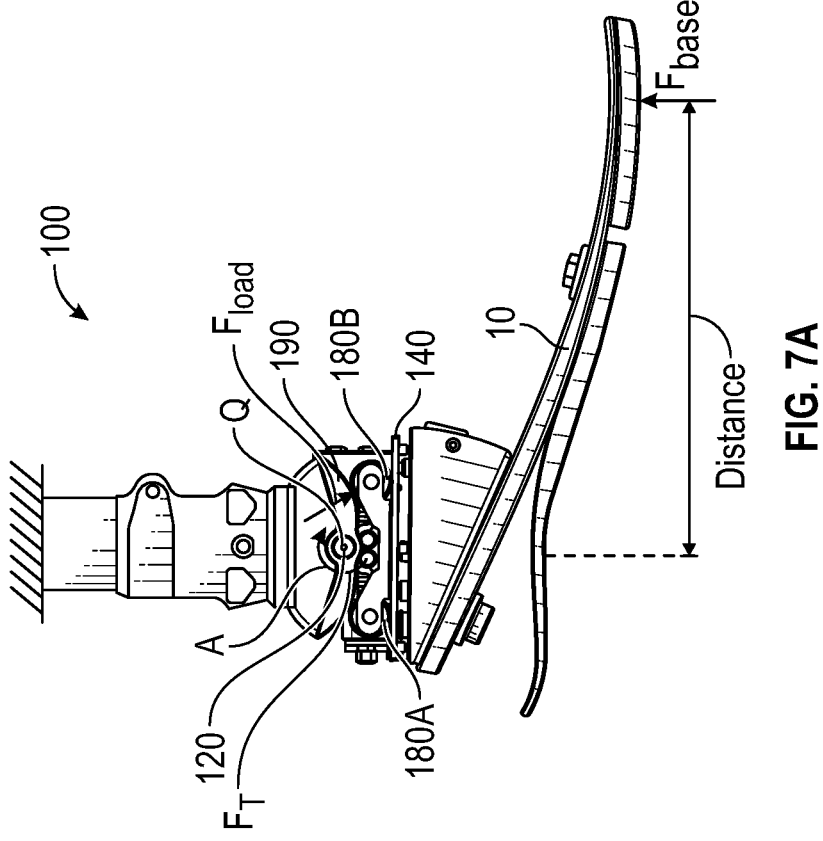

When the ankle joint 120 is bearing load in the loaded state (such as when the person is applying weight on the ankle and the foot or weight bearing), shown in FIGS. 5C, 7A and 7B, the ankle prosthesis 100 is typically not actively re-positioning. A load on the toe of the ankle prosthesis 100, referred to as ground reaction force, will induce a reaction torque $F_T$ directed in the clockwise or counterclockwise direction A or B about the ankle joint 120 related to the magnitude of the load and the distance of the load from the ankle axis (FIGS. 7A and 7B). This torque induces a force from the cam followers 190A and 190B onto the cam rollers 180A-D. This force includes both a downward force component $F_y$ in the second direction S and a lateral force component $F_x$ in the first or opposite second lateral direction C or D. During the loaded state, when the downward force component $F_y$ is greater than the preload applied upward in the first direction R by the biasing component 188, the biasing component 188 will begin to compress and the slider collar 184 and outer roller 182 will slide in the second direction S against the shaft 186 until the outer roller 182 makes contact with the roller track 140 (as shown in the right frame of FIG. 4). The ankle's sustained loads are thus guided directly into the roller track 140, and to the structural frame 104 associated with the roller track 140. This effectively changes the load path from a low friction, low stiffness path, to a shorter high friction, high stiffness path FIG. 7B). In particular, in the loaded configuration, the outer roller 182 is effectively jammed between the cam follower 190 and the roller track 140.

As can be seen in FIG. 7B, when the cam roller 180 makes contact with the roller track 140, the downward force component $F_y$ from the cam follower 190, minus the compressive force of the biasing component 188, is supported completely by the roller track 140 which applies an opposing force $F_{Base}$. In addition, friction between the cam follower 190 and the cam roller 180, as well as the friction between the cam roller 180 and the roller track 140, produces a jamming effect, which sustains the lateral force component $F_x$. Due to the coefficient of friction between these components, the lateral force component $F_x$ is resisted by this jamming effect. This ensures that components that normally would need to sustain these heavy loads, such as the roller carrier 196 and its linear bearing 197 as well as components of the actuator 106, are isolated.

The load directing mechanism 181 is illustrated as using a leaf spring as a biasing component 188. Other biasing, compliant components may be used as the biasing component 188 instead of the leaf spring, provided that the components can behave in the same fashion and have the same characteristics, as the leaf spring. The biasing component 188 needs to be strong enough to keep the cam roller 180 from shifting away from the cam follower 190 during active positioning of the ankle prosthesis 100 in the unloaded state, and compliant enough to allow the cam roller 180 to close the air gap shown in FIG. 5B when the ankle prosthesis 100 is subjected to ground reaction forces that would back-drive or damage the actuation system.

The main benefit of a cam transmission 108 is to direct the vertical force component from the cam follower 190 into the structural frame 104 of the ankle prosthesis 100, away from the components of the actuator 106. However, without the addition of the load directing mechanism 181 described herein, the roller carrier 196 and linear bearing 197 must also support this vertical load. Additionally, the horizontal load must be supported by the roller carrier 196, the leadscrew nut 166, the leadscrew 164 and its support bearings 168. During typical gait, these vertical and horizontal loads can be as great as 8500 and 5300 Newtons, respectively (1900 and 1200 lbs), requiring very strong components to withstand these loads. By changing the load path with the addition of the load directing mechanism 181, both of these loads can be supported directly by the structural frame 104 through the cam roller 180. Only the roller track 140, cam follower 190 and cam roller 180, which experience the highest forces, need to be made of a stronger material. Components of the actuator 106 can be sized purely for unloaded operation as they will not need to withstand the high loads during weight bearing. For example, because the linear bearing 197 supports only small forces and moments, it can take the form of a thin strip of plastic with low friction properties.

The cam roller 180 is free to rotate on the linear bearing 197, increasing the efficiency of the cam transmission 108. Without the load directing mechanism 181, the cam roller 180 would slide against the cam follower 190, which are in some embodiments both made from steel. As the coefficient of friction of steel sliding on steel is high, the resulting friction losses would decrease the efficiency of the ankle prosthesis 100. In the design of the present application, the cam roller 180 spins or slides on a low friction bronze bushing and rolls against the steel cam follower 190. The coefficient of friction of steel sliding on bronze is lower than steel on steel. Additionally, the coefficient of friction of steel rolling on steel is much lower than steel sliding on steel, which produces less friction losses than the ankle prosthesis 100 having a cam transmission 108 without the load directing mechanism 181 and thus increases efficiency.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

The invention claimed is:

1. A semi-active ankle prosthesis, comprising:
    an ankle prosthesis including:
        a structural frame;
        an ankle joint operatively mounted on the structural frame that pivots with respect to the structural frame about an ankle axis;
        a cam transmission including a cam follower, wherein the cam transmission pivots the ankle joint about the ankle axis;
        an actuator operatively coupled to the cam transmission to cause lateral translation of the cam transmission; and
        a load directing mechanism defined along a cam roller of the cam transmission that directs a load imposed upon the ankle prosthesis into the structural frame during a loaded state, the load directing mechanism accommodating an unloaded state and a loaded state;
    wherein in the unloaded state the cam roller is biased with an upward bias force applied in a first direction such that the cam roller contacts the cam follower and an air gap is defined between the cam roller and the structural frame, and
    wherein in the loaded state the cam roller is compressed between the cam follower and the structural frame such that the load imposed upon the ankle prosthesis exceeding the upward bias force is directed into the structural frame.

2. The semi-active ankle prosthesis of claim 1, wherein the load directing mechanism includes a biasing component that biases the cam roller of the cam transmission against the cam follower of the cam transmission.

3. The semi-active ankle prosthesis of claim 2, wherein the load directing mechanism further includes a slider collar and a shaft in association with the cam roller and the biasing component, the slider collar positioned within a coaxial channel defined within the cam roller and including a slot defined coaxially therethrough, the shaft housed within the slot, and the biasing component positioned between the shaft and a first surface of the slot.

4. The semi-active ankle prosthesis of claim 3, wherein the shaft of the load directing mechanism defines a square profile and wherein the slot of the slider collar defines a rectangular profile such that the slider collar is moveable in a second direction when the biasing component is compressed between the shaft and the first surface of the slot.

5. The semi-active ankle prosthesis of claim 2, wherein the biasing component applies the upward bias force to the cam roller such that the cam roller contacts a curved surface of the cam follower and the cam roller is lifted above a track of the structural frame when in the unloaded state.

6. The semi-active ankle prosthesis of claim 5, wherein the cam roller is operable for unimpeded rotation about a rotational roller axis by the curved surface of the cam follower when in the unloaded state.

7. The semi-active ankle prosthesis of claim 2, wherein the cam follower applies a load force to the cam roller in a second direction when in the loaded state, wherein the load force is associated with the load placed on the ankle and wherein the load force includes a downward load component and a lateral load component.

8. The semi-active ankle prosthesis of claim 7, wherein the biasing component is compressed in the second direction by the downward load component applied to the cam roller when the downward load component exceeds the upward bias force applied to the cam roller by the biasing component.

9. The semi-active ankle prosthesis of claim 8, wherein the cam roller is actuated in the second direction by the cam follower such that the cam roller contacts a track of the structural frame when the biasing component is compressed.

10. The semi-active ankle prosthesis of claim 5, wherein the track of the structural frame includes a high coefficient of friction such that rotation of the cam roller is impeded by the track of the structural frame when in the loaded state.

11. The semi-active ankle prosthesis of claim 1, wherein the cam transmission comprises a roller carrier, a first cam roller and a second cam roller carried by the roller carrier; and the cam follower operatively associated with the first cam roller and the second cam roller and pivotable about the ankle axis.

12. The semi-active ankle prosthesis of claim 11, wherein a ground force applied at a toe-end of the ankle prosthesis generates a reaction torque force directed in a first clockwise or counterclockwise direction about the ankle axis.

13. The semi-active ankle prosthesis of claim 12, wherein the reaction torque force induces a load force including a downward component in a second direction and a lateral component in a first lateral direction or an opposite second lateral direction that is applied to the first cam roller or the second cam roller by the cam follower, wherein the ankle prosthesis assumes the loaded state when the downward component exceeds the upward bias force associated with the first or second cam roller.

14. The semi-active ankle prosthesis of claim 12, wherein the first cam roller or the second cam roller is actuated in the second direction such that the first cam roller or the second cam roller contacts a track of the structural frame.

15. The semi-active ankle prosthesis of claim 1, wherein the actuator includes a motor and a leadscrew rotatable by the motor.

16. The semi-active ankle prosthesis of claim 15, wherein the leadscrew of the actuator is in operative association with a roller carrier of the cam transmission such that the actuator causes lateral movement of the roller carrier in a first or opposite second lateral direction when the ankle prosthesis is in the unloaded state.

17. The semi-active ankle prosthesis of claim 16, wherein lateral movement of the roller carrier in a first lateral direction causes rotation of the cam follower in a first clockwise or counterclockwise direction about the ankle axis and wherein lateral movement of the roller carrier in a second lateral direction causes rotation of the cam follower in an opposite second clockwise or counterclockwise direction about the ankle axis.

18. The semi-active ankle prosthesis of claim 17, wherein the cam transmission includes a first cam roller and a second cam roller, wherein the first cam roller and the second cam roller are each biased by a biasing component of the load directing mechanism in a first direction when in the unloaded state such that the first cam roller and the second cam roller contact the cam follower.

19. The semi-active ankle prosthesis of claim 18, wherein the lateral movement of the roller carrier in the first lateral direction causes the first cam roller to direct a first roller force to the cam follower in the opposite second lateral direction such that the cam follower is consequently rotated about the ankle axis in the first clockwise or counterclockwise direction, and wherein the lateral movement of the roller carrier in the opposite second lateral direction causes the second cam roller to direct a second roller force to the cam follower in the first lateral direction such that the cam follower is consequently rotated about the ankle axis in the opposite second clockwise or counterclockwise direction.

* * * * *